(12) United States Patent
Shimizu et al.

(10) Patent No.: US 6,335,007 B1
(45) Date of Patent: Jan. 1, 2002

(54) COLLAGEN GEL

(75) Inventors: Yasuhiko Shimizu, 39-676, Kohataogurayama, Uji-shi, Kyoto, 611-0002 (JP); Yukinobu Takimoto, Kyoto (JP)

(73) Assignees: Yasuhiko Shimizu, Kyoto; Tapic International Co., Ltd., Tokyo, both of (JP)

( * ) Notice: Subject to any disclaimer, the term of this patent is extended or adjusted under 35 U.S.C. 154(b) by 0 days.

(21) Appl. No.: 09/424,495

(22) PCT Filed: May 26, 1998

(86) PCT No.: PCT/JP98/02281

§ 371 Date: Nov. 24, 1999

§ 102(e) Date: Nov. 24, 1999

(87) PCT Pub. No.: WO98/54224

PCT Pub. Date: Dec. 3, 1998

(30) Foreign Application Priority Data

May 28, 1997 (JP) .............................................. 9-138904

(51) Int. Cl.[7] .......................... A61K 31/74; A61K 9/14; A61F 13/00
(52) U.S. Cl. ................... 424/78.08; 424/422; 424/484; 514/801; 514/944
(58) Field of Search ............................... 424/400, 78.01, 424/278.1, 484, 78.08, 422, 486, 485; 514/801, 944

(56) References Cited

U.S. PATENT DOCUMENTS

| 4,582,865 A |   | 4/1986 | Balazs et al. |
| 5,487,895 A | * | 1/1996 | Dapper et al. ........... 424/278.1 |
| 5,807,581 A | * | 9/1998 | Rosenblatt et al. ......... 424/484 |

FOREIGN PATENT DOCUMENTS

| EP | 0 089 145 |   | 6/1987 |
| JP | 56161046 | * | 12/1981 |
| JP | 56-161046 | * | 12/1981 |
| JP | 2-145600 |   | 5/1990 |
| JP | 7-163860 |   | 6/1995 |

\* cited by examiner

*Primary Examiner*—Thurman K. Page
*Assistant Examiner*—Blessing Fubara
(74) *Attorney, Agent, or Firm*—Peter F. Corless; Christine C. O'Day; Edwards & Angell, LLP

(57) ABSTRACT

The present invention relates to a collagen gel, its production process, a medical material in which it is used or a kit for its production, wherein said collagen gel is obtained by crosslinking collagen with polyanion and carbodiimide.

9 Claims, No Drawings

COLLAGEN GEL

TECHNICAL FIELD

The present invention relates to a collagen gel, its production process, a medical material in which it is used or a kit for its production.

BACKGROUND ART

Medical materials in the form of hemostyptics or adhesives for living body must be provided with general requirements including rapid adhesion in the presence of water, adhesion at body temperature and normal pressure, being able to be sterilized and absence of histotoxicity, able to adequately stop bleeding on wound surfaces, and being flexible after curing and not inhibiting healing. Different adhesives have been used clinically as conventional materials that satisfy these requirements to a certain extent, examples of which include synthetic adhesives such as cyanoacrylate compounds such as methyl-2-cyanoacrylateor isobutyl-2-cyanoacrylate, and polyurethane having an isocynate group at the terminal, and natural adhesives such as fibrin paste that promotes wound healing by forming insoluble fibrin from soluble fibrinogen, and gelatin-based adhesives in which gelatin is crosslinked with formaldehyde or resorcinol. In addition, Japanese Provisional Patent Publication No. 7-163860 describes a gelatin-based adhesive in which gelatin and polyanion are crosslinked with carbodiimide.

Cyanoacrylate adhesives have the shortcoming of the tissue opening up again after several days once it has been adhered, as a result that cell dies due to robbing the tissue of water during polymerization, that adhesion procedure is difficult due to the rapid reaction rate, that it is required one year to be absorbed into the tissue due to the hard reaction product formed following adhesion, and that the adhered site lacks flexibility in the manner of living body tissue (see Ikada, Y. et al. ed., Biocompatible Materials, Japan Standards Association, 1993, p. 117)., thereby worsening the wound, and the problem of tissue damage caused by formaldehyde that is formed accompanying decomposition. Isocyanate adhesives had the shortcoming of requiring considerable time for the wound surface to return to normal as a result of remaining in the tissue for one year or more. Although fibrin pastes solve the inherent shortcoming of synthetic adhesives of foreign body reactivity with the tissue, their adhesive strength is somewhat weak and have a complex procedure as a result of having to mix 2 or 4 liquids before use. Moreover, since the material is of human blood origin, there is the risk of HIV, HBs or other viral infection. In addition, since the fibrin begins to dissolve 2–3 days after applied to the wound site and is absorbed into the tissue, despite having to adhere the wound site for a fixed period of time, there was the problem of cases in which the absorption of fibrin paste was faster than healing of the wound (see Pharma Medica's off-print, Pharma Medica Vol. 14, 1996, Medical Review Publishing, p. 157).

Gelatin-based adhesives used in the clinical steps have a limited range of use due to toxicity of the formaldehyde or resorcinol used as crosslinking agent. In addition, although the invention of Japanese Provisional Patent Publication No. 7-163860 uses a crosslinking agent having low toxicity, this invention had such shortcomings that it is typically necessary to adjust consistency by heating an aqueous gelatin solution used as the material to 40° C. or higher during the production of these gelatin-based adhesives, considerable time is required for gelation in order to crosslink the short gelatin molecules,and it is required to use a large amount of crosslinking agent.

DISCLOSURE OF INVENTION

The present invention provides a material suitable for use as a medical material that is adhered easily, has powerful adhesive strength, eliminates the risk of viral infection, has low toxicity for the living body, forms an elastic adhesive layer after curing, and conversely promotes wound healing without impairing healing due to being absorbed and decomposed in the tissue.

Based on the fact that a hydrogel obtained by mixing polyanion and water-soluble carbodiimide with collagen that is commonly added to pharmaceuticals and foods exhibits high adhesiveness with living body tissue even in the presence of water, the inventors of the present invention found that this hydrogel can be applied to the living body as a non-formed medical material such as adhesive for living body, hemostyptic, obstruent or dead space filler, and/or that formed articles of this gel can be applied to the living body as a formed medical material such as blood vessel substitute and so forth, thereby leading to completion of the present invention.

Namely, the present invention relates to a collagen gel obtained by crosslinking collagen with polyanion and carbodiimide and its production process, and more particularly, to a production process of a collagen gel comprising adding water-soluble carbodiimide to an aqueous solution containing collagen and polyanion followed by crosslinking the collagen and polyanion, or by reacting olyanion and water-soluble carbodiimide in an aqueous solution containing both and adding an aqueous solution of collagen to this followed by crosslinking the collagen with polyanion. Alternatively, the present invention relates to medical materials comprised of this collagen gel, including adhesive for living body, hemostyptic, obstruent, dead space filler and medical formed articles such as blood vessel substitute, or a kit for producing those materials.

The collagen used in the present invention is collagen such as Type I, Type III or Type I+III collagen that has been removed of the strongly antigenic telopeptide portion either by, for example, alkaline treatment of insoluble collagen extracted from various animals, or by treating with enzyme such as pepsin, trypsin, chymotrypsin, papain or pronase. There are no particular restrictions on the origin of the collagen, and typically collagen can be used that is obtained from the skin, bone, cartilage, tendon or organs, etc. of birds or mammals such as cows, pigs, rabbits, sheep and mice. Differing from gelatin, since this collagen allows the obtaining of a suitable consistency without heating, preparation can be made easily in the case of gelation. In addition, since this collagen has a higher molecular weight than gelatin, it more closely resembles living body tissue, has considerable physiological activity, and therefore promotes healing in the case of using on a wound, resulting in a favorable contrast to the tendency of gelatin to conversely inhibit tissue regeneration. This collagen is flexible after curing and requires only a short time for crosslinking, in other words, requires only a short time for gelation. Collagen is used by dissolving in a non-toxic solvent with respect to the living body, examples of which include water, physiological saline, a buffer such as borate buffer, or an aqueous solution containing a salt such as sodium chloride, sodium bromide and potassium bromide, or protein, sugar or lipid, etc.

The polyanion used in the present invention is a polymer that is water-soluble and has numerous carboxyl groups as functional groups. It may be polymer originated from living body or synthetic polymer provided it has a low level of toxicity with respect to the living body. Specific examples include hyaluronic acid, alginic acid, gum arabic, polyglutamic acid, polyacrylic acid, polyaspartic acid, polymalic acid, carboxymethylcellulose and carboxylated starch. Since the molecular weight of these polyanions has an effect on the adhesiveness of the gel during collagen gel formation or on the hardness after curing and so forth, it is arbitrarily decided as desired. These polyanions are used by dissolving in an aqueous solvent having low toxicity with respect to the living body similar to that used to dissolve the collagen. In addition, the concentration of polyanion aqueous solution is suitably determined according to the viscosity of the aqueous solution or the number of carboxyl groups possessed by one polymer molecule, etc.

Examples of water-soluble carbodiimides preferably used in the present invention include 1-ethyl-3-(3-dimethylaminopropyl) carbodiimide hydrochloride and 1-cyclohexyl-3-(2-morpholinyl-4-ethyl)carbodiimide sulfonate. Since the water-soluble carbodiimides used in the present invention change into inactive, water-soluble urea derivatives accompanying reaction, the resulting collagen gel has an extremely low level of toxicity. These water-soluble carbodiimides are used either directly in the form of powders, or by dissolving in a solvent that is not toxic to the living body similar to that used to dissolve collagen or polyanion.

The collagen gel of the present invention is formed either by adding water-soluble carbodiimide to an aqueous solution containing collagen and polyanion and mixing, or by reacting polyanion with water-soluble carbodiimide followed by mixing collagen aqueous solution into the resulting aqueous solution. The following provides an explanation of these steps. Furthermore, this step may be performed on a wound at the affected site to which it is to be applied.

As an example of a process for forming a gel by adding water-soluble carbodiimide to an aqueous solution containing collagen and polyanion, if 0.5–20 parts or more of a 0.1–50 wt %, and preferably 0.5–25 wt %, aqueous solution of water-soluble carbodiimide, or 2 parts of water-soluble carbodiimide powder, are added to 100 parts of a mixed aqueous solution containing 0.1–3 wt %, and preferably 0.25–1 wt %, of collagen, and 0.1–10 wt %, and preferably 0.5–5 wt %, of polyanion, polymerization occurs in a matter of seconds resulting in gelation.

In this manner, by adding carbodiimide at a suitable concentration to collagen and polyanion, amide bonds or ester bonds are formed between the carboxyl groups in the polyanion molecule and the amino groups or hydroxyl groups in the collagen molecule, resulting in the occurrence of crosslinking between or within the collagen and polyanion molecules followed by gelation.

The product of adding water-soluble carbodiimide to an aqueous solution containing collagen and polyanion may be left to stand as is, or it may be stirred.

The temperature and time in the case of gelation by adding water-soluble carbodlimide to an aqueous solution containing collagen and polyanion are 10–40° C. and 5–120 seconds, respectively.

In addition, as an example of a process for forming a gel by reacting polyanion and water-soluble carbodiimide in an aqueous solution containing both followed by mixing with a collagen aqueous solution, polyanion and carbodiimide are first reacted by adding 100 parts or more of a 0.1–20 wt % aqueous solution of water-soluble carbodiimide, or water-soluble carbodiimide powder, to 100 parts of a 0.2–20 wt % aqueous solution of polyanion.

Carboxyl groups in the polyanion molecule are converted to acid anhydride bonds by the above-mentioned reaction.

In this manner, in the case of reacting polyanion and carbodiimide in an aqueous solution containing both, the product of adding carbodiimide to polyanion may be allowed to stand as is, or it may be stirred. The temperature and time in the case of reacting polyanion and carbodiimide are 10–40° C. and 1–5 minutes, respectively.

Next, collagen gel is formed in a matter of seconds by mixing 1–100 parts of the reaction solution obtained by reacting carbodiimide with polyanion according to the above-mentioned process with 1–200 parts, and preferably 5–100 parts, of a 0.1–3 wt % aqueous solution of collagen.

In this manner, by mixing collagen with polyanion in which the carboxyl groups have been converted to acid anhydride bonds, the acid anhydride bonds in the polyanion molecule react with functional groups such as carboxyl groups, amino groups or hydroxyl groups in the collagen molecule, resulting in the formation of amide bonds or ester bonds between or within the collagen and polyanion molecules followed by the formation of a gel.

The amount of time required for gelation by mixing collagen with polyanion in which the carboxyl groups have been converted to acid anhydride bonds is 5–120 seconds. The temperature during mixing in 10–40° C.

Collagen gel of the present invention obtained by the above-mentioned processes can be used as various medical materials, examples of which include adhesives for living body used during adhesion of incision wounds of the dura mater, peritoneum or fascia, etc., adhesion of bone or cartilage, adhesion of parenchymatous organ incisions, adhesion of skin, use during anastomosis of nerve, intestine or uterine tube, or in cases of the attachment of skin grafts or wound protective covering materials.

Since the collagen gel of the present invention forms a gel even in the presence of moisture such as that in blood or humor, and demonstrates a high degree of adhesiveness with respect to living body tissue, it can be used as a hemostyptic for the purpose of stopping bleeding from microvessels of parenchymatous organs during surgery and the leakage of blood from suture holes during suturing, and as an occluding material for stopping the leakage of humor such as pulpal liquid or bile etc., blocking openings during eardrum deficit, occluding blood vessel substitute, blocking air leakage holes following lung surgery, occluding bronchi and occlusion for living body or medical occlusion including sealing of shunt tubes.

Moreover, the collagen gel of the present invention can also be used as a dead space filler by filling dead spaces such as wound cavities in bone and cartilage and alveolar cavities following tooth extraction.

In addition, another embodiment of the present invention provides a kit composed of (1) collagen aqueous solution, (2) polyanion aqueous solution, and (3) carbodiimide aqueous solution for simply and quickly obtaining collagen gel during surgery and other applications.

The collagen gel of the present invention can also be as a medical formed article having weak immunogenecity and satisfactory strength, examples of which include formed medical materials such as artificial blood vessels, artificial tubes for nerve and artificial esophagus, for the purpose of the collagen portion being absorbed into the living body after a fixed amount of time by forming into a tube, sheet, mesh, suture, plate, rod or film, etc., and either using this formed article alone or combining with the use of an artificial material, followed by applying to the human body in a manner of a transplantation and so forth.

In the case of using the collagen gel of the present invention as an adhesive, hemostyptic, occluding material or dead space filler, the collagen gel of the present invention prepared in advance is either coated and/or filled into the affected area, or an aqueous solution of collagen gel material is prepared separately as described below and applied and/or filled into the affected area directly.

Examples of methods for coating the collagen gel of the present invention to the affected area include two layer or multi-layer application methods, methods in which the two liquids described below are dropped on to the affected area and mixed coating methods such as spraying, such as (1) a method in which an aqueous solution containing collagen, polyanion and water-soluble carbodiimide mixed in advance is coated onto the affected area, (2) a method in which separately prepared collagen aqueous solution and an aqueous solution containing polyanion reacted with carbodiimide are coated onto the affected area, and (3)a method in which a mixed aqueous solution of collagen and polyanion and a water-soluble carbodiimide aqueous solution are coated onto the affected area.

Methods for filling the collagen gel of the present invention into dead spaces include filling each of the respective liquids into the dead space in compliance with the above-mentioned methods (1) through (3).

Collagen gel formed at the affected area in this manner can be formed into a film, lump or other shape according to the particular purpose, and is able to maintain its shape at the time of coating or filling into the affected area. In addition, the thickness of the collagen gel or the surface area covered and so forth can be changed as desired by changing the amount coated or amount filled.

Next, the following provides a detailed explanation of the present invention through its examples. These examples do not limit the present invention in any way whatsoever.

BEST MODE FOR CARRYING OUT THE INVENTION

EXAMPLE 1

0.1 ml of a 100 mg/ml aqueous solution of polyglutamic acid was mixed with 1 ml of a 1 wt % aqueous hydrochloric acid solution of enzyme-extracted pig skin collagen (pH 3.0) at a room temperature of 25° C. and used as Liquid A. Next, a 200 mg/ml aqueous solution of water-soluble carbodiimide was prepared and used as Liquid B. As a result of mixing 1 ml of Liquid A with 0.1 ml of Liquid B at a room temperature of 25° C., the mixture solidified and lost fluidity in 10 seconds.

EXAMPLE 2

0.1 ml of a 250 mg/ml aqueous solution of polyglutamic acid was mixed with 1 ml of a 1 wt % aqueous hydrochloric acid solution of enzyme-extracted pig skin collagen (pH 3.0) at a room temperature of 25° C. and used as Liquid A. Next, a 100 mg/ml aqueous solution of water-soluble carbodiimide was prepared and used as Liquid B. As a result of mixing 1 ml of Liquid A with 0.1 ml of Liquid B at a room temperature of 25° C., the mixture solidified and lost fluidity in 10 seconds.

EXAMPLE 3

An artificial blood vessel was produced using the method of Examples 1 and 2. Teflon rods having a diameter of 4 mm and glass tubes having an inner diameter of 6 mm were each made available. A Teflon rod was stood upright in each glass tube, and each Liquid A prepared in Examples 1 and 2 was filled around it. Next, an amount of each Liquid B equal to one-tenth the amount of Liquid A was dropped in. When the aqueous collagen solution gelled after 30 seconds and the Teflon rod was removed, a firm collagen tube having an inner diameter of 4 mm was obtained in both cases.

EXAMPLE 4

0.1 ml of a 100 mg/ml aqueous solution of polyglutamic acid was mixed with 1 ml of a 0.5 wt % aqueous hydrochloric acid solution of enzyme-extracted pig skin collagen (pH 3.0) at a room temperature of 25° C. and used as Liquid A. Next, a 200 mg/ml aqueous solution of water-soluble carbodiimide was prepared and used as Liquid B. As a result of mixing 1 ml of Liquid A with 0.1 ml of Liquid B at a room temperature of 25° C., the mixture solidified and lost fluidity in 10 seconds.

EXAMPLE 5

0.1 ml of a 100 mg/ml aqueous solution of polyglutamic acid was mixed with 1 ml of a 0.25 wt % aqueous hydrochloric acid solution of enzyme-extracted pig skin collagen (pH 3.0) at a room temperature of 25° C. and used as Liquid A. Next, a 200 mg/ml aqueous solution of water-soluble carbodiimide was prepared and used as Liquid B. As a result of mixing 1 ml of Liquid A with 0.1 ml of Liquid B at a room temperature of 25° C., the mixture solidified and lost fluidity in 20 seconds.

EXAMPLE 6

A skin incision wound on the back of a rat was adhered using collagen gels prepared according to the methods of Examples 4 and 5. An vertical incision of 1 cm was made in the skin on the back of the rat using a scalpel under general anesthesia. 1 ml of Liquid A and 0.1 ml of Liquid B were dropped onto the incision wound to adhere the incision wound. The incision wound was firmly adhered after 20 seconds. When the healing state was observed 3 days, 5 days, 7 days, 2 weeks and 3 weeks after surgery, the incision wound continued to remain adhered at all times, and the wound healed in 2 weeks.

What is claimed is:

1. A process for producing a collagen gel comprising adding water-soluble carbodiimide to an aqueous solution containing collagen and polyanion, and crosslinking the collagen with the polyanion, wherein said polyanion is selected from a group consisting of alginic acid, gum arabic, polyglutamic acid, polyacrylic acid, polyaspartic acid, polymalic acid, carboxymethyl cellulose or carboxylated starch, and wherein crosslinking of the collagen with the polyanion and carbodiimide is affected in 5–120 seconds at 10–40° C.

2. The production process according to claim 1 wherein said aqueous solution containing collagen and polyanion is an aqueous solution containing 0.25–1 wt % of collagen and 0.5–5 wt % of polyanion, and said collagen gel is obtained by adding 0.5–20 parts of a 0.5–25 wt % aqueous solution of water-soluble carbodiimide, or 2 parts of water-soluble carbodiimide powder, to 100 parts of said mixed aqueous solution.

3. A process for producing a collagen gel comprising reacting polyanion and water-soluble carbodiimide in an aqueous solution containing them, adding an aqueous solution of collagen, and crosslinking the collagen with the polyanion, wherein said polyanion is selected from a group consisting of alginic acid, gum arabic, polyglutamic acid, polyacrylic acid, polyaspartic acid, polymalic acid, carboxymethyl cellulose or carboxylated starch, and wherein crosslinking of the collagen with the polyanion and carbodiimide is affected in 5–120 seconds at 10–40° C.

4. The production process according to claim 3 wherein said reaction solution of polyanion and water-soluble carbodiimide is obtained by adding at least 100 parts of a 0.1–20 wt % aqueous solution of water-soluble carbodiimide, or water-soluble carbodiimide powder, to 100 parts of a 0.2–20 wt % aqueous solution of polyanion, and said collagen gel is obtained by mixing 1–100 parts of said reaction solution of polyanion and water-soluble carbodiimide with 5–100 parts of a 0.1–3 wt % aqueous solution of collagen.

5. A medical material comprising a collagen gel, wherein the collagen gel is obtained by crosslinking collagen with polyanion and water-soluble carbodiimide according to the process of claims 2 or 4.

6. The medical material according to claim 5 wherein said medical material is an adhesive for living body, hemostyptic, obstruent or dead space filler.

7. The medical material according to claim 5 wherein said medical material is an artificial blood vessel, artificial tube for nerve or artificial esophagus.

8. A kit for producing a collagen gel comprising (1) collagen aqueous solution, (2) polyanion aqueous solution, and (3) carbodiimide aqueous solution, wherein said polyanion is selected from a group consisting of alginic acid, gum arabic, polyglutamic acid, polyacrylic acid, polyaspartic acid, polymalic acid, carboxymethyl cellulose or carboxylated starch, and wherein the collagen gel is obtained by crosslinking collagen with polyanion and water-soluble carbodiimide according to the process of claims 2 or 3.

9. A collagen gel obtained by the process of claims 1 or 3.

* * * * *